(12) United States Patent
Schiff et al.

(10) Patent No.: US 11,730,951 B2
(45) Date of Patent: Aug. 22, 2023

(54) SYSTEM AND METHOD FOR MODULATING SPREADING DEPRESSION AND STATE-BASED CONTROL

(71) Applicant: The Penn State Research Foundation, University Park, PA (US)

(72) Inventors: Steven J. Schiff, State College, PA (US); Bruce J. Gluckman, State College, PA (US); Andrew J. Whalen, Levittown, PA (US)

(73) Assignee: The Penn State Research Foundation, University Park, PA (US)

( * ) Notice: Subject to any disclaimer, the term of this patent is extended or adjusted under 35 U.S.C. 154(b) by 335 days.

(21) Appl. No.: 16/763,366

(22) PCT Filed: Nov. 9, 2018

(86) PCT No.: PCT/US2018/059963
§ 371 (c)(1),
(2) Date: May 12, 2020

(87) PCT Pub. No.: WO2019/094681
PCT Pub. Date: May 16, 2019

(65) Prior Publication Data
US 2020/0297994 A1 Sep. 24, 2020

Related U.S. Application Data

(60) Provisional application No. 62/584,836, filed on Nov. 12, 2017.

(51) Int. Cl.
*A61N 1/05* (2006.01)
*A61N 1/36* (2006.01)
*A61N 1/20* (2006.01)
*A61N 2/00* (2006.01)
*A61N 2/02* (2006.01)

(52) U.S. Cl.
CPC ............. *A61N 1/0529* (2013.01); *A61N 1/20* (2013.01); *A61N 1/36025* (2013.01); *A61N 1/36031* (2017.08); *A61N 1/36064* (2013.01); *A61N 2/006* (2013.01); *A61N 2/02* (2013.01)

(58) Field of Classification Search
CPC .... A61N 1/0529; A61N 1/20; A61N 1/36025; A61N 1/36031; A61N 1/36064; A61N 2/006; A61N 2/02; A61N 1/0476; A61N 2/06
See application file for complete search history.

(56) References Cited

U.S. PATENT DOCUMENTS

| | | | | |
|---|---|---|---|---|
| 5,938,689 A | * | 8/1999 | Fischell | ............. A61N 1/36185 607/45 |
| 6,402,678 B1 | * | 6/2002 | Fischell | ................... A61N 2/02 600/13 |
| 2010/0152811 A1 | | 6/2010 | Flaherty | |

(Continued)

OTHER PUBLICATIONS

Anderson, 2002, Journal of Neurophysiology, 88(5), 2713-2725.
(Continued)

*Primary Examiner* — Mark W. Bockelman
(74) *Attorney, Agent, or Firm* — Riverside Law LLP

(57) ABSTRACT

The present invention provides devices and methods for modulating spreading depression in the brain.

20 Claims, 13 Drawing Sheets

(56) References Cited

U.S. PATENT DOCUMENTS

2015/0265830 A1    9/2015  Simon
2018/0085000 A1*   3/2018  Weffers-Albu ...... A61B 5/7282

OTHER PUBLICATIONS

Bikson et al., 2001, The Journal of Physiology, 531(1), 181-191.
Brinley et al., 1960, Journal of Neurophysiology, 23(3), 246-56.
Canals et al., Oct. 2005, Journal of Neurophysiology, 94(2), 943-51.
Chen, Shih-Pin, et al. "Vagus nerve stimulation inhibits cortical spreading depression." Pain 157.4 (2016): 797.
De Luca and Bures, 1977, Developmental Psychobiology, 10(4), 289-97.
Gluckman et al., 1996, Journal of Neurophysiology, 76(6), 4202-5.
Gluckman et al., 2001, The Journal of Neuroscience, 21(2), 590-600.
Grafstein, 1956, Journal of Neurophysiology, 19(2), 154-71.
Grafstein, 1956, Journal of Neurophysiology, 19(4), 308-16.
Huang et al., 2004, The Journal of Neuroscience, 24(44), 9897-902.
Kager et al., 2002, Journal of Neurophysiology, 88(5), 2700-12.
Koroleva and Bures, 1979, Brain Research, 173(2), 209-15.
Koroleva and Bures, 1980, Electroencephalography and Clinical Neurophysiology, 48(1), 1-15.
Lauritzen et al., 2011, Journal of Cerebral Blood Flow and Metabolism, 31(1), 17-35.
Lauritzen, 1994, Brain : A Journal of Neurology, 117 ( Pt 1, 199-210.
Leao, 1944, J Neurophysiol, 7, 359-390.
Makarova et al., 2008, The European Journal of Neuroscience, 27(2), 444-56.
Purpura and Malliani, 1966, Brain Research, 20 1(4), 403-6.
Purpura and McMurtry, 1965, Journal of Neurophysiology, 28(1), 166-85.
Reddy and Bures, 1980, Neuroscience Letters, 17(3), 243-247.
Tottene et al., 2009, Neuron, 61 (5), 762-73.
Wei et al., 2014, The Journal of Neuroscience, 34(35), 11733-43.

* cited by examiner

Intrinsic optical signal:
increased brightness represents increasing depolarization Intracellular K+ dye:
decreased brightness represents intracellular decrease of potassium

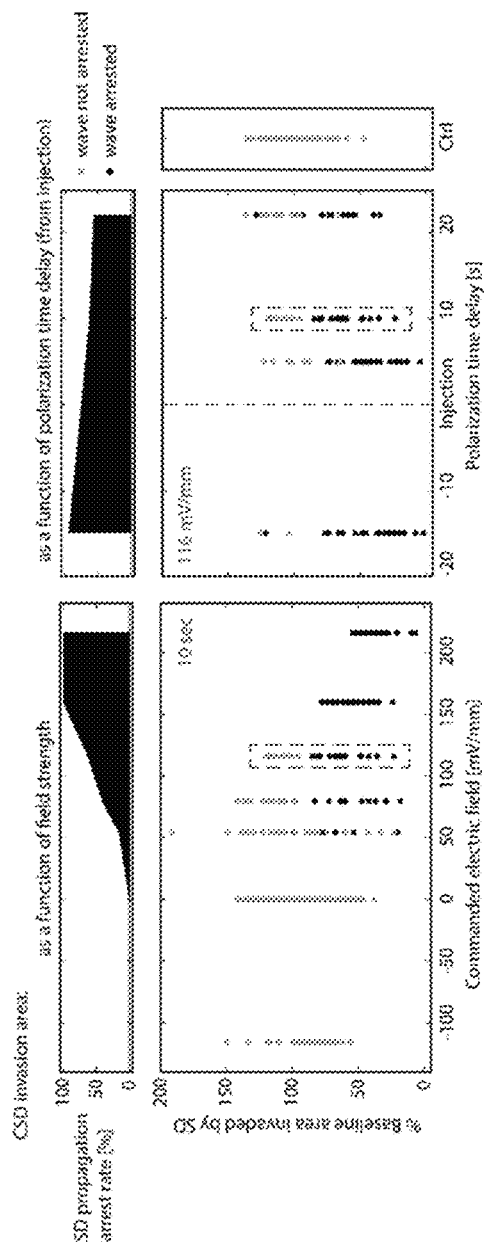
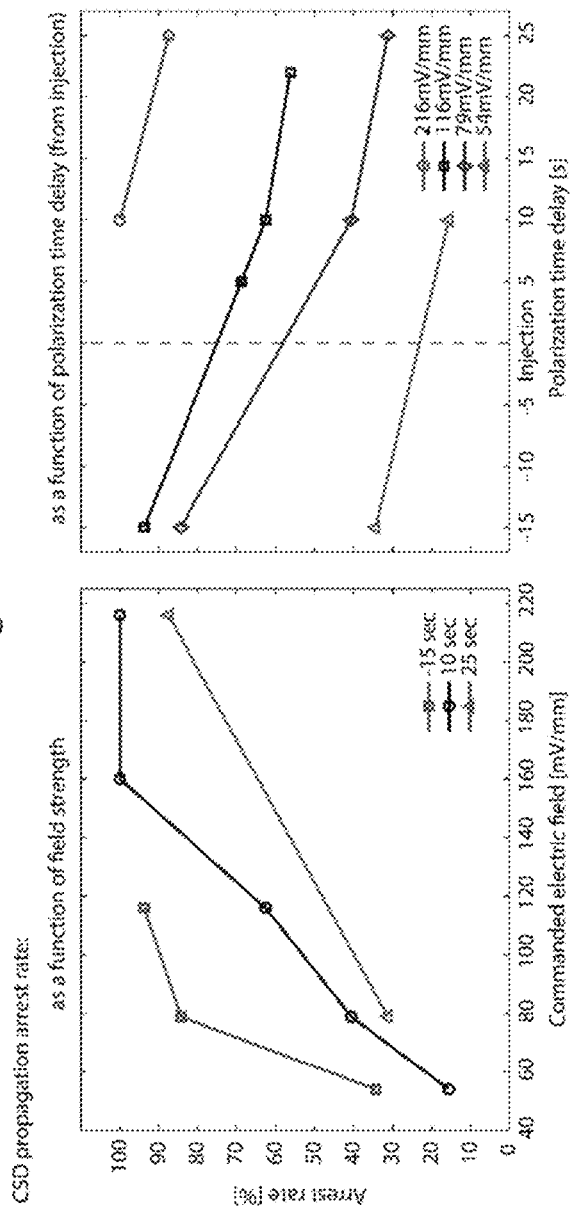
Fig. 3C
Fig. 3D

SYSTEM AND METHOD FOR MODULATING SPREADING DEPRESSION AND STATE-BASED CONTROL

CROSS-REFERENCE TO RELATED APPLICATIONS

This application is a '371 National Phase Entry of PCT Application No. PCT/US18/59963, filed Nov. 9, 2018, which claims priority to U.S. Provisional Patent Application No. 62/584,836, filed on Nov. 12, 2017, both of which are incorporated herein by reference in their entireties.

STATEMENT REGARDING FEDERALLY SPONSORED RESEARCH OR DEVELOPMENT

This invention was made with government support under Grant No. EB014641 awarded by the National Institutes of Health. The Government has certain rights in the invention.

BACKGROUND OF THE INVENTION

First observed by Aristides Ledo in the cortex of anesthetized rabbits (Leao, 1944, J Neurophysiol, 7, 359-390), spreading depression (SD) is a large-scale pathological brain phenomenon related to migraine, stroke, hemorrhage and traumatic brain injury (Lauritzen, 1994, Brain: A Journal of Neurology, 117 (Pt 1, 199-210; Lauritzen et al., 2011, Journal of Cerebral Blood Flow and Metabolism, 31(1), 17-35). Once initiated, spreading depression propagates across grey matter extruding potassium and other active molecules, collapsing the resting membrane voltage gradient of cells leading to spike inactivation and cellular swelling, and propagates independently of synaptic transmission.

It manifests as a slow (2-5 mm/min) traveling wave front of neuronal depolarization. The wave front can trigger transient seizures as it encounters fresh brain tissue, and leaves in its wake transiently inactivated and swollen brain tissue. The underlying dynamics of SD are generally regarded as the physiological mechanism of the initial aura in human migraines (Lauritzen, 1994, Brain: A Journal of Neurology, 117 (Pt 1, 199-210). Recent work has demonstrated that there is a unification possible in the modeling of the biophysics of spikes, seizures, and SD, and that each of these dynamics occur within a different state of the neuronal membrane (Wei et al., 2014, The Journal of Neuroscience, 34(35), 11733-43). Importantly, computational modeling suggests that the ignition of SD is thought to be linked to currents flowing inward through the apical dendrites of neurons (Kager et al., 2002, Journal of Neurophysiology, 88(5), 2700-12; Makarova et al., 2008, The European Journal of Neuroscience, 27(2), 444-56), as opposed to the soma during action potential spike generation.

In pioneering early work, Grafstein found that polarization of the cortical tissue parallel to the direction of a propagating SD wave increased the conduction velocity of SD when the polarization direction was positive to negative in the direction of propagation (Grafstein, 1956, Journal of Neurophysiology, 19(2), 154-71; Grafstein, 1956, Journal of Neurophysiology, 19(4), 308-16). This suggested that the propagation is mediated by the movement of positively charged ions such as potassium. While surface repetitive pulse stimulation has been shown to interfere with the propagation of SD (Grafstein, 1956, Journal of Neurophysiology, 19(2), 154-71; Grafstein, 1956, Journal of Neurophysiology, 19(4), 308-16; Koroleva and Bures, 1980, Electroencephalography and Clinical Neurophysiology, 48(1), 1-15), the effects of transcortical DC polarization on SD have not been systematically explored.

Thus, there is a need in the art for devices and methods for modulating SD. The present invention satisfies this unmet need.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1, comprising FIG. 1A: Schematic of the feedback-controlled electric field modified perfusion chamber and coronal slice somatodendtiric axis alignment with the applied transcortical field. Local high $K^+$ is injected from the top pipette (purple) to initiate SD. Example control output of the PID feedback field controller (FIG. 1B), commanding a 116 mV/mm field in the tissue. Inset depicts the slight overshoot performance upon field step on. FIG. 1C shows a schematic of a series of 3-epoch experiments consisting of control, polarization, followed by repeat control runs, so that the effect of recovery following induction of multiple SDs and the effect of stimulation are accounted for. FIG. 1D shows a schematic of the simultaneous intrinsic optical signal and potassium epifluorescence imaging configuration, utilizing a Dual View multichannel imaging system (Photometrics, Tucson, Ariz.). An example output of the configuration is shown in FIG. 1E. FIG. 1F: Simultaneous IOS (red) and APG-2 intracellular potassium dye epi-fluorescence (blue) signals are shown individually, and with overlap (bright pink overlay) indicating that the intracellular K+ decrease during the SD wave is along the leading edge of the IOS signal.

FIG. 2, comprising FIG. 2A: Electric field effects (116 mV/mm) on the propagation and invasion of SD into the various layers of coronal slices imaged via IOS. Normal SD propagation through all cortical layers during a control trial (left). SD propagation under surface negative DC polarization confines the spread to the superficial cortical layers (middle), while SD propagation was forced into the deeper layers of the cortex and arrested by surface positive DC polarization (right). FIG. 2B: Corresponding timing of SD signal as a function of cortical depth and time, the color bar representing light intensity changes as percent of baseline for the line of pixels indicated in red in upper plots (lower row in FIG. 2A).

FIG. 3, comprising FIG. 3A through FIG. 3D, depicts the results of modulation experiments. FIG. 3A: Summary of SD propagation velocity differences as a percentage of the averaged control trials for +/−116 mV/mm electric field strengths as a function of field polarity. The significant differences (p<0.01, n=52) between groups are marked by asterisks, outliers are open circles. FIG. 3B: SD propagation velocity as a function of each type of 3-epoch experiment (control with either positive or negative polarization) for +/−116 mV/mm electric field strength. The flanking control trials for each polarization are shown here separately, while the grey dividing line indicates the independence between positive and negative experimental trials. The significant differences (p<0.01, n=52) between groups are marked by asterisks, outliers are open circles. FIG. 3C: Dose response of field strength efficacy (bottom left), and polarization timing from initiation of injection (bottom right) in arresting SD propagation (arrest % rate plotted above, n=32). Each distribution plotted for a different field strength and a different polarization timing (for the 116 mV/mm field), compares the area of cortical tissue invaded by SD expressed as a percentage of the control trial SD invasion area. Black dots in the distribution indicate trials where the horizontal SD propagation was arrested by the applied field, gray dots indicate trials where the wave did not stop. Stronger fields and earlier polarizations are more effective in minimizing the tissue area affected by SD. The control trial is plotted separately for comparison (bottom far right). FIG. 3D: Dose response of field strength (left) and polarization delay time (right) efficacy in arresting SD propagation (% arrest rate, n=32). Curves plotted for different polarization delay times with respect to high $K^+$ injection at time t=0. The time delay of the polarization response on the SD arrest rate is consistent across field strengths—the earlier the polarization is applied to the SD wave the more effective the arrest rate. Preconditioning the tissue with polarization before SD induction via KCl injection shows the most effective arrest rates for each field strength tested. The effectiveness of stopping SD was related to the strength of the applied field at all delay times.

FIG. 4, comprising FIG. 4A depicts a diagram of a tangential cortical slice and neuron body orientation demonstrating the typical propagation of SD and the near isotropic nature of tangential slices. FIG. 4B depicts an intrinsic optical signal (IOS) recorded in tangential slices comprising a fast SD propagation related intensity peak followed by a slower recovery signal component. FIG. 4C depicts an IOS signal of ring wave propagation in tangential slices, darker color represents increasing depolarization.

DETAILED DESCRIPTION

Definitions

Figure 1A:
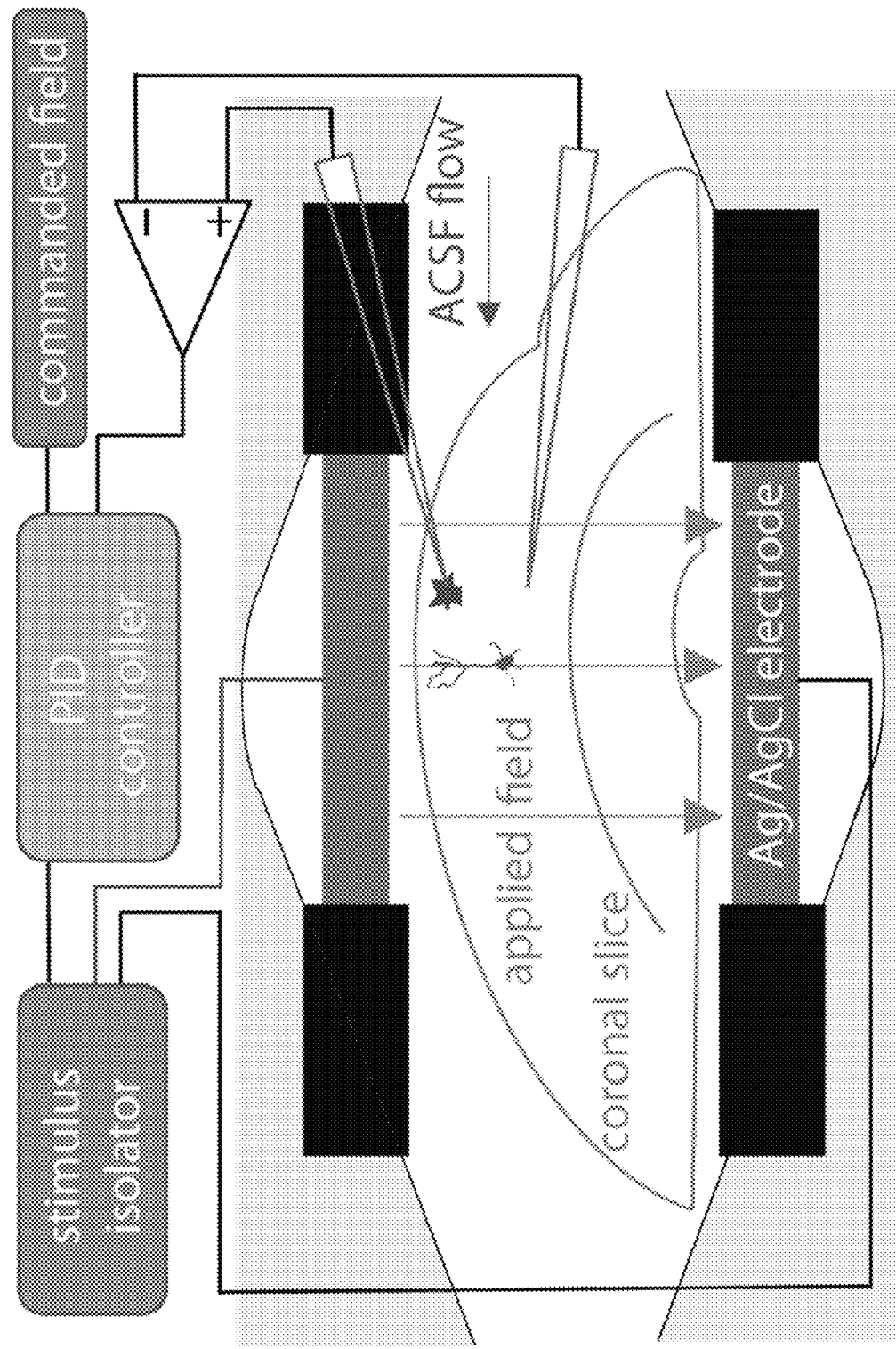
FIG. 1A through FIG. 1F, is a series of schematics depicting the experiments described herein.
Figure 1B:
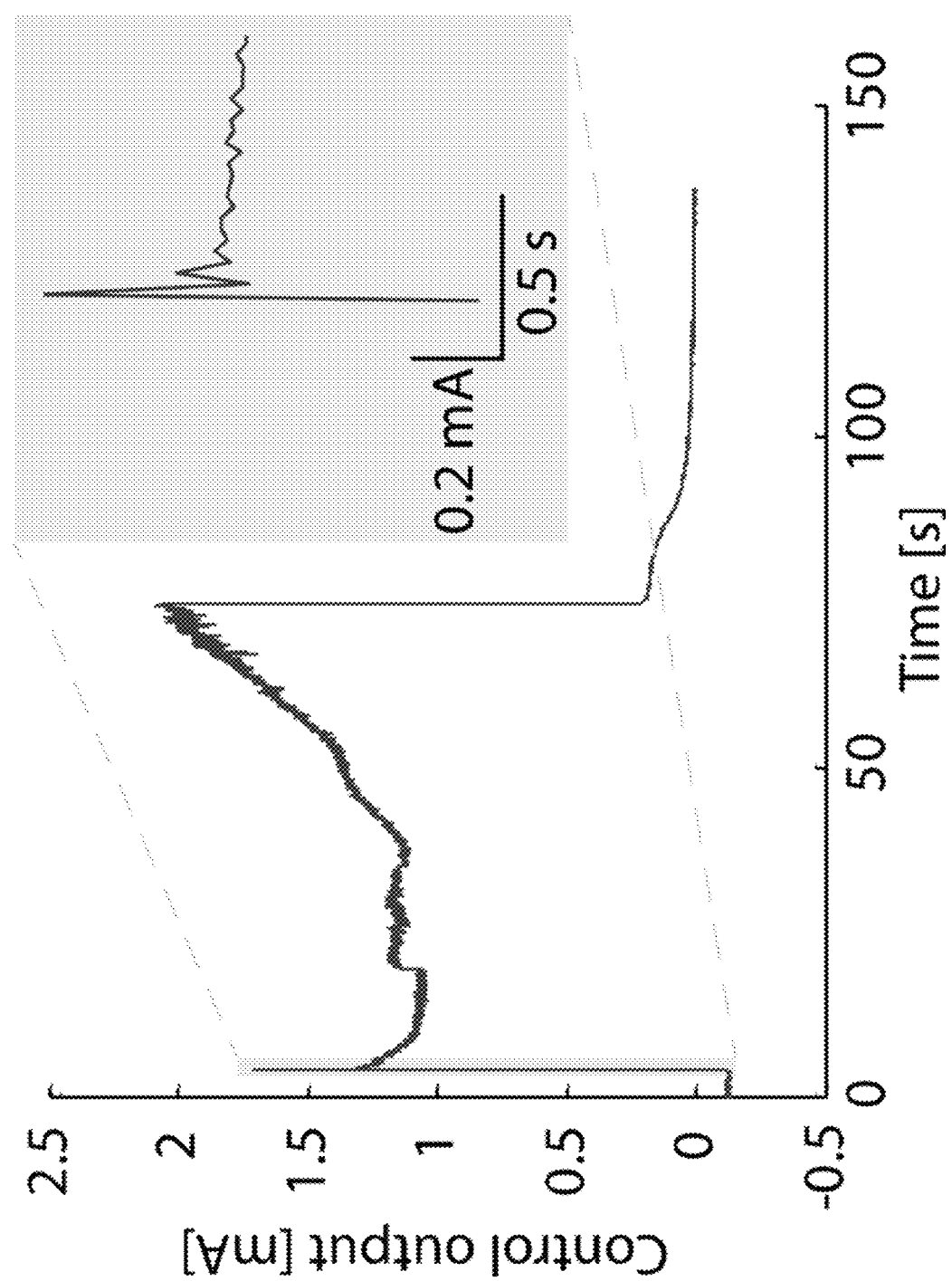

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to devices, systems, and methods to modulate spreading depression (SD) in the brain of a subject. For example, the present invention relates to the ability to modulate the velocity of a SD wave and the extent of SD wave propagation. In certain aspects, the invention relates to the ability to arrest an SD wave. Accordingly, the present invention provides for devices, systems, and methods for treating or preventing a disorder associated with SD, including, but not limited to, migraine, stroke, hemorrhage, ischemia, hypoxia, seizures, epilepsy, and traumatic brain injury.

Throughout this disclosure, the terms "spreading depression", "SD", and "spreading depolarization" are used interchangeably, as would be understood by a person skilled in the art from the context in which they are presented.

The present invention is based, in part, upon the discovery that externally applied transcortical DC electric fields and electrical currents can modulate SD. For example, it is demonstrated herein that electric fields and currents can suppress, confine, and arrest SD. The ability to modulate SD using externally applied stimuli provides for devices and methods for the invasive and non-invasive treatment and prevention of disorders associated with SD.

In one embodiment, the present invention provides a method of modulating SD, wherein the method prevents SD initiation, slows SD wave propagation, arrests SD wave propagation, and/or confines the spread of SD. In one embodiment, the method comprises administering a stimulation to the brain, or portion thereof, thereby modulating SD. In certain embodiments, the administered stimulation comprises an electric current, electric field, or currents induced by a magnetic field. In certain embodiments, the stimulation can be applied prior to the development of SD. In certain embodiments, the stimulation can be applied during SD wave propagation.

The stimulation may be triggered, for example by detection of one or more signals or properties indicating that SD is likely to occur or that SD is occurring in the brain. In certain embodiments, the stimulation is triggered by a subject being treated or by a health care provider. For example, the stimulation may be triggered by the subject or health care provider when a subject is exhibiting signs or symptoms of a disorder associated with SD. In certain embodiments, the stimulation parameters are modulated based upon the detection of one or more properties of the brain used to determine the state of the brain.

In one embodiment, the method comprises administering an electrical stimulus to the brain or brain region to modulate SD. In one embodiment, the method comprises positioning one or more electrodes in the vicinity of the brain, and supplying current or voltage to the one or more electrodes, thereby administering the electrical stimulus and generating electric current and shaping an electric field. The electrodes may be positioned internally or externally. For example, in certain embodiments, one or more electrodes are positioned internally, where the electrodes are inserted into or onto brain tissue. In certain embodiments, one or more electrodes are positioned externally, where electrodes are positioned on the scalp, within the skull, or beneath the skull in the epidural or subdural spaces. In one embodiment, the method comprises the use of one or more transcortical DC electrodes. In certain embodiments, the one or more electrodes are placed at locations to modulate activity in the frontal, parietal, occipital, or temporal lobes of the brain. For example, in one embodiment, a constant current is applied to the one or more DC electrodes thereby creating an electric current. In another embodiment, a constant voltage is applied across two or more DC electrodes, thereby creating an electric field.

In certain embodiments, the electric field stimulation is in the range of about 100 μV/mm to about 500 mV/mm. In one embodiment, the electric field stimulation is in the range of about 1 mV/mm to about 250 mV/mm.

In certain embodiments, the strength of the administered electric field can vary depending on the condition of the subject or the detected state of the brain.

In certain embodiments, the method comprises administering a constant stimulation to the brain. For example, the stimulation may be administered for a duration of seconds, minutes, hours, days, or years. In certain embodiments, the method comprises administering a pattern of stimulation, for example in a pulsatile, oscillatory, or sinusoidal pattern, to the brain. In certain embodiments, the stimulation is administered in a sinusoidal pattern at a frequency in the range of about 1-10,000 Hz.

The stimulation may be administered before or after SD initiation. For example, it is demonstrated herein that stimulation prior to SD initiation is highly effective in preventing or arresting SD wave propagation. In certain embodiments, the stimulation is administered after determination that SD initiation is likely to occur, but before SD initiation has begun. For example, the stimulation may be administered in the range of about 10 minutes to 0.1 seconds prior to SD initiation. In certain embodiments, the stimulation is administered after SD initiation. For example, in one embodiment, the stimulation is administered in the range of about 0.1 seconds to 10 minutes after SD initiation.

In certain embodiments, the method comprises administering either a positive or negative polarization stimulus to the brain. For example, as described herein surface positive and surface negative polarization may differentially modulate SD propagation. In one embodiment, the method comprises tailoring the polarization, timing, or strength of the stimulation to best treat or prevent the SD-associated disorder in the subject.

In one embodiment, the method comprises positioning one or more magnets or electromagnets in the vicinity of the brain thereby exposing the brain to an alternating magnetic field. The one or more magnets or electromagnets may be positioned internally or externally. Oscillating magnetic fields induce electrical currents in the brain. The use of magnetic fields can have advantages in that the skull does not attenuate them as much as it does electrical fields, and thus the sources of magnetic fields (electromagnets or moving fixed magnets) can be positioned in locations less invasive to the brain itself (such as within or on the skull). For example, in certain embodiments, one or more magnets or electromagnets are positioned internally, where the magnets or electromagnets are inserted into or onto brain tissue. In certain embodiments, one or more magnets or electromagnets are positioned externally, where magnets or electromagnets are positioned on the scalp, within the skull, or beneath the skull in the epidural or subdural spaces.

In certain embodiments, the method comprises measuring one or more electrical or biochemical properties of the brain to assess the state of the brain. For example, the method may comprise measuring the one or more properties to determine that the brain is functionally normal or at steady state; in the state of SD; and/or in the state of seizures.

In various embodiments, determining the state of the brain may comprise measuring neuronal network activity, membrane potential, the presence or abundance of biomarkers, or the like. In one embodiment, the method comprises detecting the electrical signals from one or more regions of the brain through the use of an electroencephalogram (EEG). The signals can be analyzed for normal or abnormal delta, theta, alpha, beta, gamma, or mu wave activity. In certain embodiments, determining the state of the brain may comprise detecting the extracellular K+ concentration, whereby local or global elevations indicate the presence or emergence of SD. This can be done with chemical or optical or electrochemical sensors. In addition, there are a wide variety of chemical biomarkers of SD that can be employed in sensing, such as adenosine, glutamate, and other metabolic compounds that signal the dynamics of SD or predict its occurrence.

In certain embodiments, the determination of the state of the brain is used to effectuate the stimulation of the brain, as described herein. For example, using one or more properties of the brain can be used to determine if stimulation is necessary, and if so, can be used to determine the pattern of stimulation, placement of electrodes, stimulation intensity, stimulation duration, polarization, or the like. In certain embodiments, the method provides a feedback system where the method comprises real-time detection of the one or more properties for the real-time control of stimulation parameters. The signals or parameters can be electrical, chemical, optical, or other modalities that signal the chemical and physical changes of the brain associated with SD.

In one aspect, the present invention provides a method of determining the state of the brain, which may include the normal or steady state; the SD state; the epileptic seizure state, or mixtures of the spreading depression and epileptic seizure state. In certain embodiments, the method of determining the state of the brain then determines the nature and timing of stimulation of the brain. For example, in certain embodiments, the nature and timing of stimulation to maintain the normal or steady state of the brain is calculated from the measured state of the brain. In one embodiment, the nature and timing of stimulation to a pathological state of the brain, such as seizures or spreading depression, is calculated from the measured state of the brain, in order to return the brain to the normal or steady state. In one embodiment, the invention provides the use of a method of determining the state of the brain that is then used to calculate the nature and timing of stimulation to a pathological state of the brain, such as seizures or spreading depression, to return the brain to the normal or steady state, in an automated feedback manner.

In certain instances, the stimulation parameters may depend upon the orientation of the neurons to be effected. For example, as described herein, when modulating SD in the cortex, where large principal neurons have their main apical dendrites pointing to the surface, surface positive polarization suppresses the propagation of SD and surface negative polarization suppresses seizure activity. To effect the hippocampus, where neurons are inverted with respect to the surface of this brain structure, surface negative polarization may be used to suppress SD while surface positive polarization may be used to suppress seizure.

Methods described herein can be used to modulate SD in any subject, including any subject having or at risk of developing a disorder associated with SD. For example, in certain embodiments, the subject has, or is at risk for developing, migraine, stroke, ischemia, hypoxia, seizure, epilepsy, traumatic brain injury, or hemorrhage. In certain embodiments, the method is used to modulate SD in a subject following brain surgery. In certain embodiments, the method is used to modulate SD in a subject having ischemia or hypoxia of the brain, due to near-drowning, asphyxiation, or the like.

The method described herein can be conducted on any species, including, but not limited to, humans, primates, horses, cows, dogs, cats, rabbits, guinea pigs, rats, mice, and the like. In certain aspects the method described herein is conducted in research settings in vivo or in cell culture or brain slice samples. For example, in certain embodiments, the method described herein can be used to modulate SD in animal or cell culture models of one or more neurologic diseases or disorders.

In one aspect, the present invention provides a device for modulating SD in the brain. For example, in certain embodiments, the device is configured for administering a stimulation, such as electric current, electric field, potential difference, and/or or magnetic field, to the brain to prevent SD initiation, slow SD wave propagation, arrest SD wave propagation, and/or confine SD spread.

In certain embodiments, the device comprises one or more electrodes suitable for delivering an electrical stimulus to the brain. For example, in one embodiment, the device comprises one or more electrodes for creating an electric field. In certain embodiments, the electrodes are biocompatible, suitable for permanent or temporary implantation in the brain or brain region. In certain embodiments, the electrodes are suitable for positioning on the scalp or head of the subject. In certain embodiments, the electrodes are DC electrodes for providing transcranial or intracranial stimulation. Electrodes can be polarizing or non-polarizing, and can have a variety of surfaces including steel, platinum, iridium, or a variety of configurations such as reaction chamber or capacitively coupled.

In certain embodiments, the device comprises one or more magnets or electromagnets for creating a magnetic field. In certain embodiments, the magnets or electromagnets are biocompatible, suitable for permanent or temporary implantation in the brain or brain region, or within or apposed to the skull. In certain embodiments, the magnets or electromagnets are suitable for positioning on the scalp or head of the subject.

In certain embodiments, the device comprises one or more additional components for delivering an electric or magnetic stimulation, including, but not limited to, a signal generator, constant current or voltage stimulator, feedback control system, amplifiers, filters, and the like.

In certain embodiments, the device comprises one or more components to determine one or more electrical or biochemical properties of the brain to determine the state of the brain. For example, in certain embodiments, the device comprises one or more electrodes (e.g., EEG electrodes) to detect the electrical activity of the brain. In certain embodiments, the device comprises one or more sensors or probes to detect the presence or abundance of one or more biomarkers that can be used to assess the state of the brain. For example, the device may comprise one or more chemical or optical or electrochemical sensors. In addition, there are a wide variety of chemical biomarkers of SD that can be employed in sensing, such as adenosine, glutamate, and other metabolic compounds that signal the dynamics of SD or predict its occurrence. In one embodiment, the device comprises a sensor or probe to detect extracellular K+.

In certain embodiments, a device of the present invention comprises a controller operably connected to the one or more electrodes or magnets. For example, in certain embodiments, the controller communicates with the signal generator, constant current stimulator, or one or more stimulatory electrodes or magnets to trigger stimulation or modulation stimulation parameters. In certain embodiments, the controller communicates with the one or more components (e.g. electrodes, sensors, probes, etc.) used to detect the electrical or biochemical properties of the brain. For example, in certain embodiments, the controller receives data related to the detected properties of the brain; analyzes the data to determine the state of the brain; and communicates with the signal generator, constant current stimulator, or stimulatory electrodes to deliver a stimulation or modulate stimulation parameters based upon the determined state of the brain.

In one embodiment, the controller is wired to the electrodes or other device components. In one embodiment, the controller is wirelessly connected to the electrodes or other device components. In one embodiment, the controller comprises a power source. For example, the controller may comprise a long-lasting battery. In another embodiment, the power source is a rechargeable power source, such as a rechargeable battery. In one embodiment, the power source is wirelessly rechargeable. The controller of the invention is not limited to any particular type of power source, but rather encompasses any type of suitable power source as would be understood by those skilled in the art.

The controller can comprise any suitable computing device including desktop or mobile devices, laptops, desktops, tablets, smartphones or other wireless digital/cellular phones, wrist watches, televisions or other thin client devices as would be understood by those skilled in the art. Further, the controller may comprise software that includes a user interface that allows for the changing of stimulation or detection settings, which can then be transmitted from the controller to the signal generator, constant current stimulator, or one or more stimulatory electrodes. Communication between the controller and the other device components can be made via any technology, including, but not limited to radio signals, near field communication systems, hypersonic signal, infrared systems, cellular signals, global system for mobile communications (GSM), and the like.

As would be understood by those skilled in the art, the device may be wirelessly connected to an expanded network through, for example, a wireless modem, wireless router, wireless bridge, and the like. Additionally, the software platform of the system may utilize any conventional operating platform or combination of platforms (Windows, Mac OS, iOS, Chrome, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access. Access or use restrictions may be implemented for users at any level. Such restrictions may include, for example, the assignment of user names and passwords that allow the use of the present invention, or the selection of one or more data types that the subservient user is allowed to view or manipulate.

In certain embodiments the network provides for data transfer from the controller to the signal generator, constant current stimulator or stimulatory electrodes, and vice versa. In certain embodiments the network provides for data transfer from the one or more components (e.g., electrodes, sensors, probes etc.) used to detect the brain properties to the controller, and vice versa. For example, data transfer can be made via any wireless based technology, including, but not limited to radio signals, near field communication systems, hypersonic signal, infrared systems, cellular signals, GSM, and the like. In some embodiments, data transfer is conducted without the use of a specific network. Rather, in certain embodiments, data is directly transferred to and from the device components via systems described above.

The software may include a software framework or architecture that optimizes ease of use of at least one existing software platform, and that may also extend the capabilities of at least one existing software platform. The software provides applications accessible to one or more users (e.g., subject, patient, health care provider) to perform one or more functions. Such applications may be available at the same location as the user, or at a location remote from the user. Each application may provide a graphical user interface (GUI) for ease of interaction by the user with information resident in the system. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. Presentation of data through the software may be in any sort and number of selectable formats. For example, a multi-layer format may be used, wherein additional information is available by viewing successively lower layers of presented information. Such layers may be made available by the use of drop down menus, tabbed pseudo manila folder files, or other layering techniques understood by those skilled in the art.

The software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a patient, doctor, nurse, emergency medical technicians, or other health care provider of the particular results.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Control of Spreading Depression with Electrical Fields

Described herein are experiments which demonstrate the effects of transcortical DC polarization on SD propagation. The effects of varying field strengths, stimulus timing and methods of SD generation are explored in conjunction with simultaneous intrinsic optical imaging and potassium dye epi-fluorescence.

The modulation, suppression and prevention of spreading depression, as measured with intrinsic optical imaging and potassium dye epifluorescence is demonstrated, utilizing applied transcortical DC electric fields in brain slices. The electric field induced forcing of spreading depression propagation to locations in cortex outside of the normal propagation path was observed, whereby further propagation is confined and arrested even after field termination. The opposite electric field polarity produces an increase in propagation velocity and a confinement of the wave to the normal propagation path. These field polarities are of opposite sign to the polarity that blocks neuronal spiking and seizures, and are consistent with biophysical models of spreading depression. The results demonstrate the potential feasibility of electrical control and prevention of spreading depression.

The materials and methods used in these experiments are now described.

Animals

Neocortical slices were obtained from male Sprague-Dawley rats aged P16 to P21. Briefly, the animals were deeply anesthetized with diethyl-ether and decapitated, the brain removed and coronal slices were sectioned from occipital neocortex. The slices were prepared differently for each of the experiments and are described in the following sections.

Slice Preparation

After decapitation, the whole brain was quickly and carefully removed to chilled (0-4° C.) artificial cerebrospinal fluid (ACSF) for 60 seconds containing the following (in mM): 126 NaCl, 2.5 KCl, 2.4 $CaCl_2$, 10 $MgCl_2$, 1.2 $NaH_2PO_4$, 18 $NaHCO_3$, and 10 dextrose. ACSF was saturated with 95% O2 and 5% $CO_2$ at room temperature for 1 hour before the dissection with an osmolality ranging from 295-310 mOsm and pH from 7.20-7.40. Coronal occipital cortical slices were cut with a vibratome on the rostro-caudal and medio-lateral coordinates of bregma −2 to −8 mm and lateral 1 to 6 mm, respectively. The first cut was made 1100 μm deep from the caudal surface and discarded, for bath applied high $K^+$ experiments 3 slices were taken from each hemisphere each 300 μm thick while for locally injected high K$^+$ experiments, 4 slices were taken from each hemisphere each 450 µm thick. Tangential slices were sectioned with the first cut made 100 µm deep from the pial surface and discarded, and a 500 µm thick slice was taken of the middle cortical layers (Huang et al., 2004, The Journal of Neuroscience, 24(44), 9897-902). After cutting, slices were transferred to a chamber containing ACSF and recovered for 30 minutes at 32-34° C. then incubated at room temperature (20-22° C.) for an additional 30 minutes prior to recording. For potassium dye loading, Asante Potassium Green-2 AM ester (Abcam) was dissolved in DMSO and 0.045% Pluronic F-127 (TEF labs) and added to the incubation ACSF for a final concentration of 20 µM, followed by 1 hour of loading and 1 hour rinsing at room temperature before imaging.

SD Generation

A schematic of the recording chamber and arrangement of electrodes is shown in FIG. 1.

For local injection induction of SD, modified ACSF (in mM) 121.25 NaCl, 6.25 KCl, 1.5 CaCl$_2$, 0.5 MgCl$_2$, 1.25 NaH$_2$PO$_4$, 25 NaHCO$_3$, and 25 dextrose was perfused over the slice at a rate of 2.8-3.0 mL/min at 30° C. during recording. To evoke SD, a pico-liter injector (PLI-10; Warner Instruments) was used to inject 3 M KCl into layer II/III using a 150 ms pulse at a pressure of 28.4 psi (which was more than sufficient to ignite robust spreading depression propagation).

For bath applied high K$^+$ induction, 26 mM KCl replaced equimolar NaCl and MgCl$_2$ was lowered to 1.3 mM. The flow of ACSF into the chamber was switched to 26 mM K+ solution; SD would typically initiate from one or more foci in layers II/III of the cortex after 1-2 minutes of exposure at which point the flow was switched back to normal ACSF. After each SD episode, the slice was allowed to recover for 15 minutes and in this way multiple SD waves could be repeatedly evoked using either method without apparent damage to the tissue.

Electric Field Application

The recording chamber (RC-22C; Warner Instruments) was fitted with Ag/AgCl sintered pellet electrodes (4.37 mm×L, 1.20 mm×H, separation distance 5.60 mm) insulated such that only the tissue in the camera's field of view would be polarized as shown in FIG. 1A. Extracellular pipettes (4-6 MΩ) were filled with 3M KCl and the injection pipette inserted into the middle top of layer II/III with the second pipette located directly inline ~900 µm in the deeper layers of the tissue near the bottom of the cortex. Differential voltage measurements were acquired (MultiClamp 700A; Axon Instruments) as a feedback measurement of the field developed inside the tissue. In order to guarantee the field strength a Labview interface was used to control a National Instruments BNC-2120 signal generator and drive voltage commands to a constant current isolated stimulator (Model 2200; AM-Systems) as in FIG. 1B. A proportional integral differential (PID) feedback control system was implemented on the differential voltage measurement measured within the cortical tissue, allowing precise and reproducible electric field strengths to be commanded for each stimulus trial.

Figure 1C:
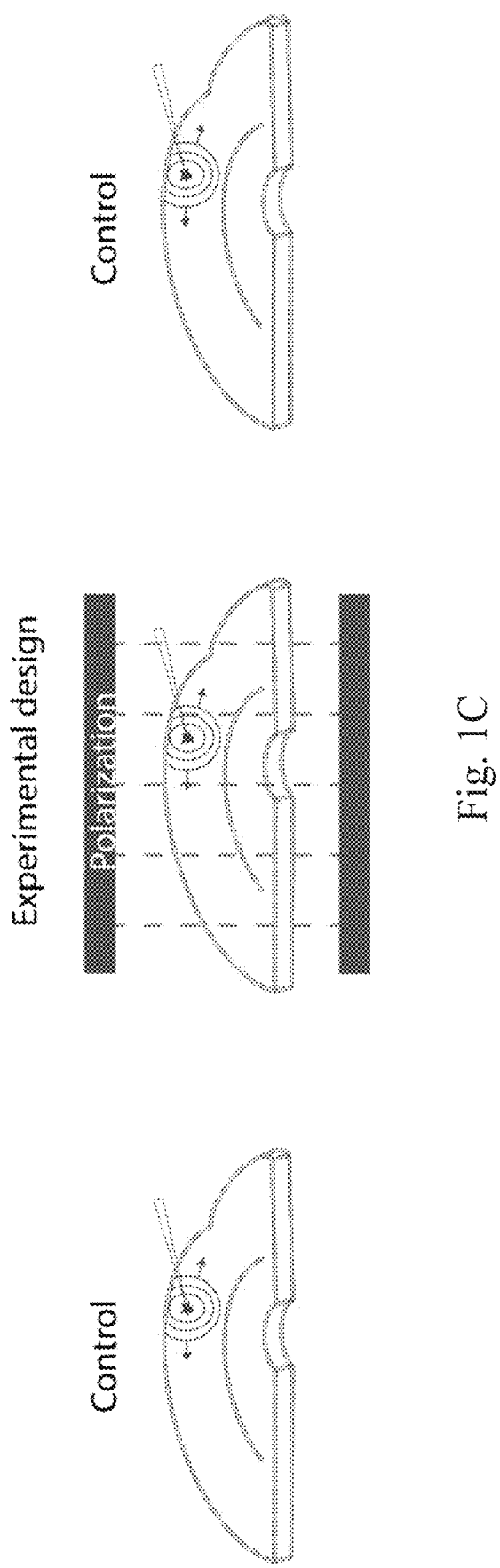
Figure 1D:
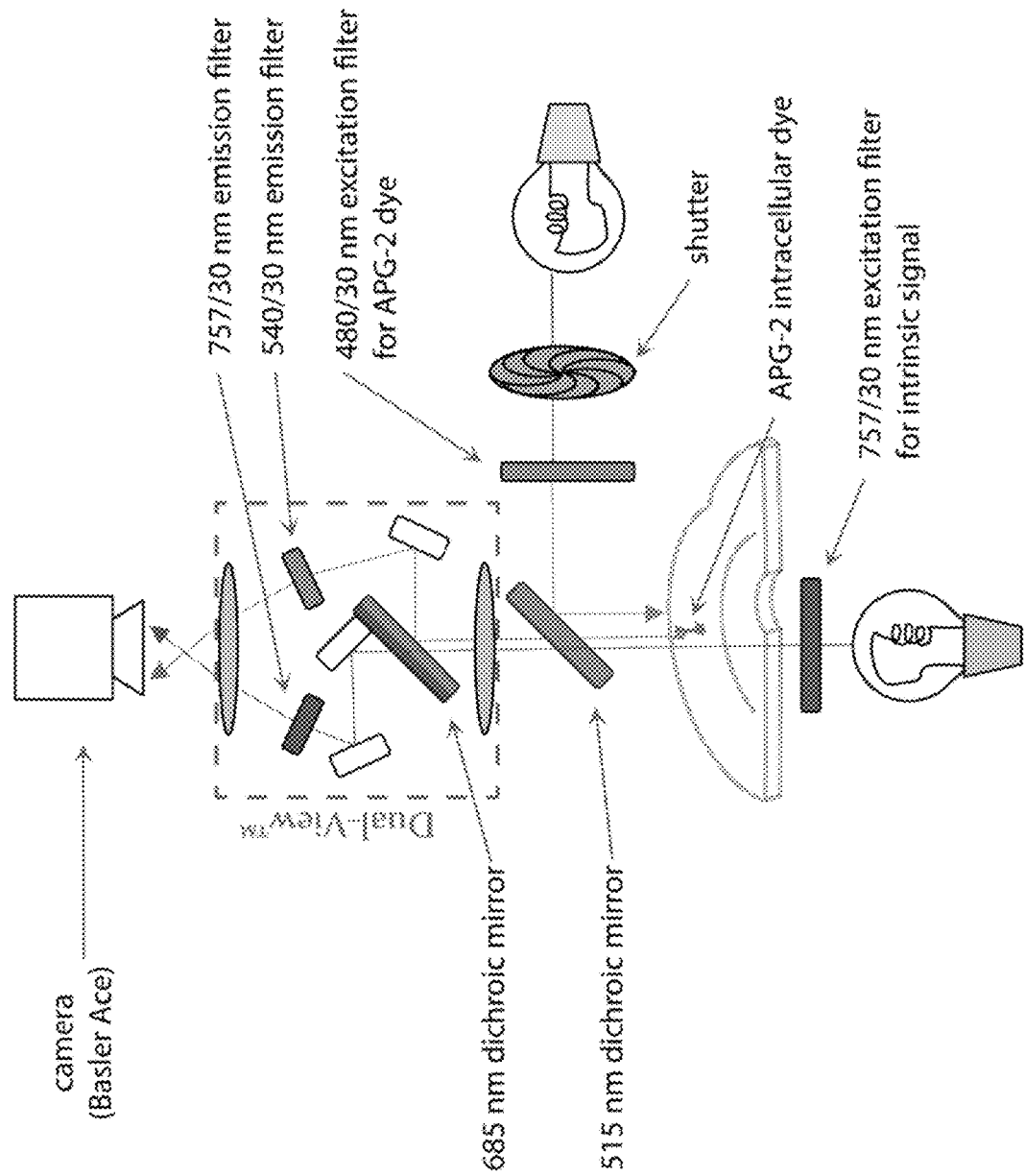
Figure 1E:
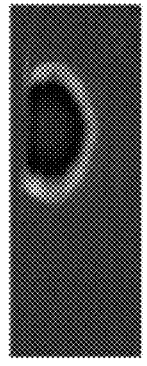
Figure 1E:
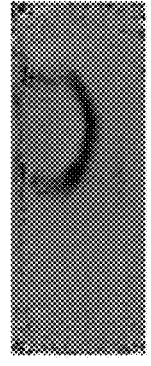
Figure 1F:
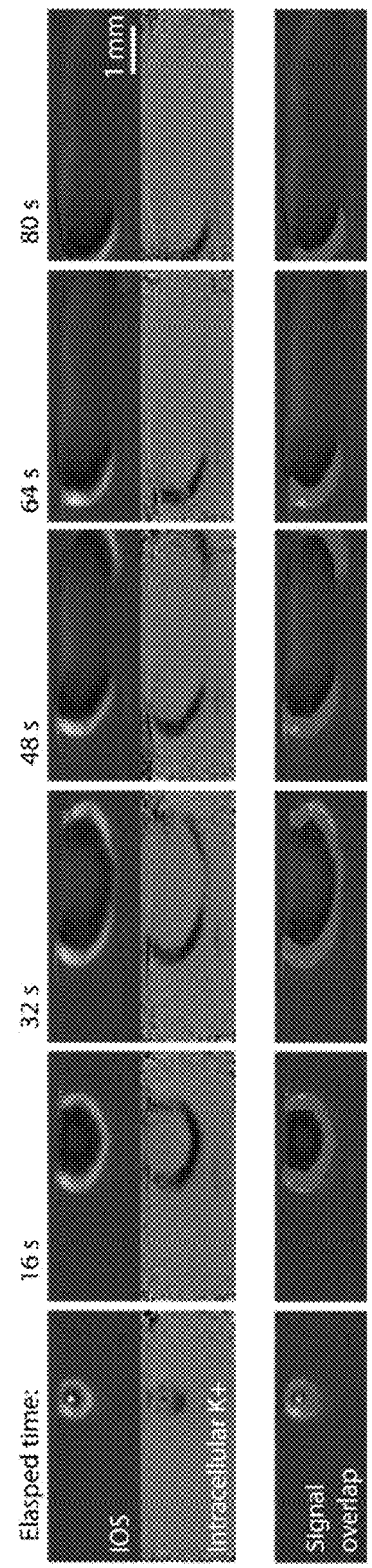

The experimental protocol was built from 3-epoch trials as shown in FIG. 1C. First a control trial was performed with no field present to assess the health and condition of the slice—any slice that appeared to be in poor condition optically or unable to propagate a strong SD signal was discarded. Slices with a strong first SD signal were allowed to recover for 15 minutes, then a second polarization trial was conducted with the electric field on, and following a second recovery period a third SD control trial was performed to ensure any effects observed in the polarization trial are related to the field. Repetitive SD episodes for any given slice were limited to these 3-epoch paradigms (one experimental trial between two controls) to ensure slice viability and maximize the number of slices utilized per experiment. Several types of experimental electric field paradigms were tested in this work, including dose responses on polarization time delay with respect to the high K$^+$ injection time, field strength amplitude, as well as negative and positive pial surface polarization trials. Each polarization trial is then compared with both control trials using 1-tailed t-tests with $p<0.01$ regarded as significant.

Spreading Depression Imaging Via the Intrinsic Optical Signal (IOS) and APG-2 Epi-Fluorescence SD was observed by measuring the changes in light transmittance through the tissue—the intrinsic optical signal (IOS) which is related to local neuronal activity and cell swelling. In the described configuration, the transmitted light of the IOS is dominated by cell swelling during SD (Anderson, 2002, Journal of Neurophysiology, 88(5), 2713-2725). Optical imaging and local field potential were recorded simultaneously during a portion of the experiments; slices were trans-illuminated with white light filtered at 757±30 nm. For simultaneous IOS and epi-fluorescence imaging, a Dual-View optical multichannel system (Photometrics, Tucson, Ariz.) was configured as in FIG. 3. Video frames were acquired with a 4× objective at 30 Hz (0.5 Hz for simultaneous IOS/epi-fluorescence, with 300 ms of illumination) using a 1296×966 pixel charge-coupled device (CCD) camera with 12-bit resolution (acA1300-30 um; Basler) which was set for 1× camera amplifier gain and stored on disk for off-line analysis. Each pixel in the images equated to a 4×4 µm square, the full resolution providing a 5.184×3.864 mm imaging window of the cortical tissue.

Data Analysis

Data were spatially filtered with a Gaussian smoother (10×10 pixel kernel) then low pass forward and reverse filtered with a 3rd order Butterworth filter at 0.25 Hz and analyzed in MATLAB (Mathworks, Natick, Mass.). The filtered time series of luminous intensity at each pixel was then analyzed for the SD peak by taking the derivative and finding the time point of maximum rate of change. This ensemble of SD peak detection time points at each pixel creates a map of where the SD peak was detected and during what time point it passed each pixel, in short a "time map" containing spatiotemporal information about the propagation of the IOS (or APG-2 dye) signals of spreading depression. From this measurement, SD propagation velocity and the extent of invasion into the tissue could be computed and further analyzed for the effects of various applied electric fields during SD propagation. All trial groups were compared using 1-tailed t-tests where $p<0.01$ was regarded as significant.

The results of the experiments are now described.

Figure 4A:
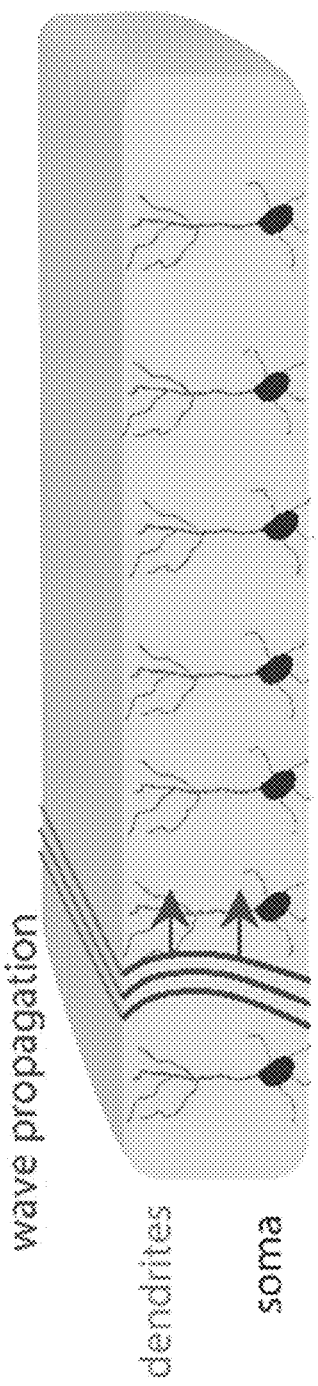
FIG. 4A through FIG. 4C, depicts SD propagation in tangential cortical slices.
Figure 4B:
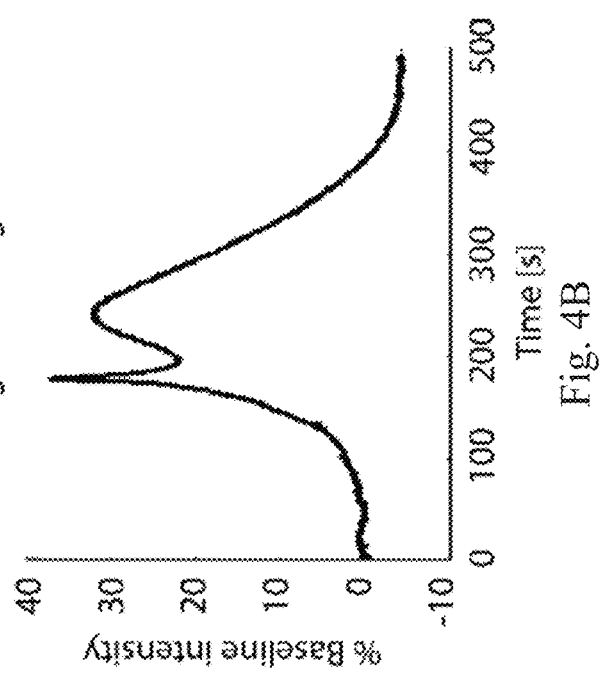
Figure 4C:
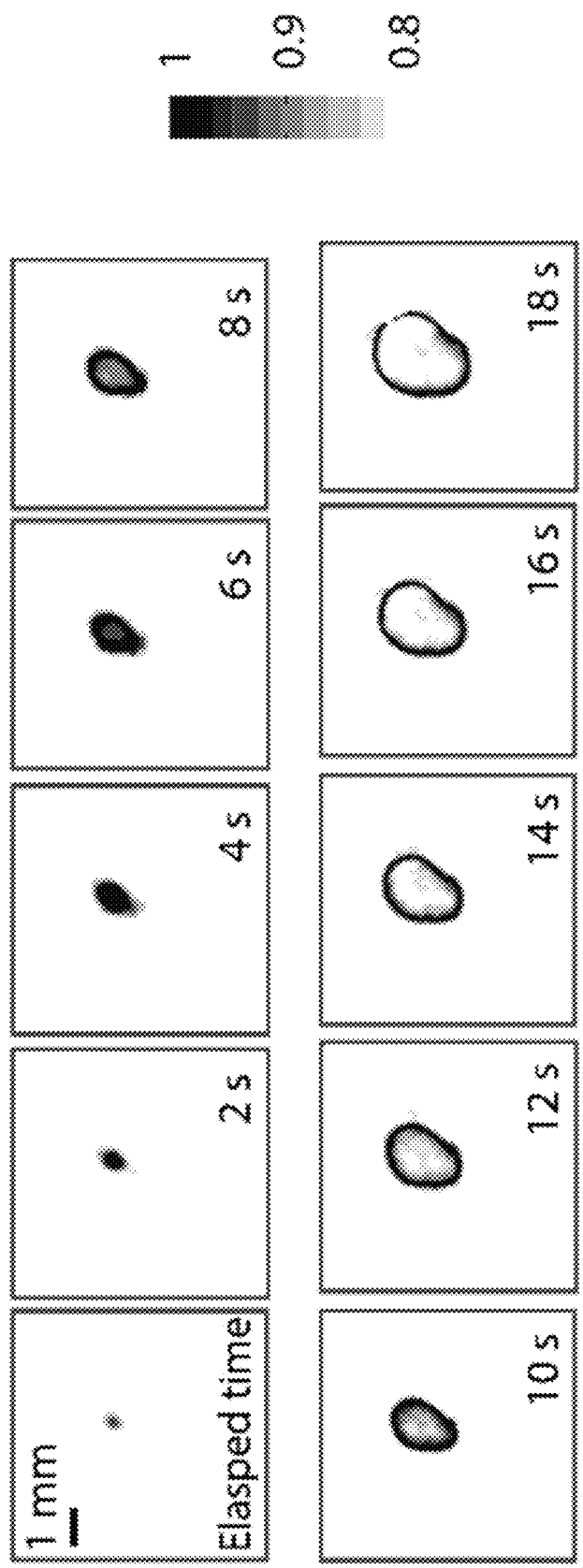
Figure 6:
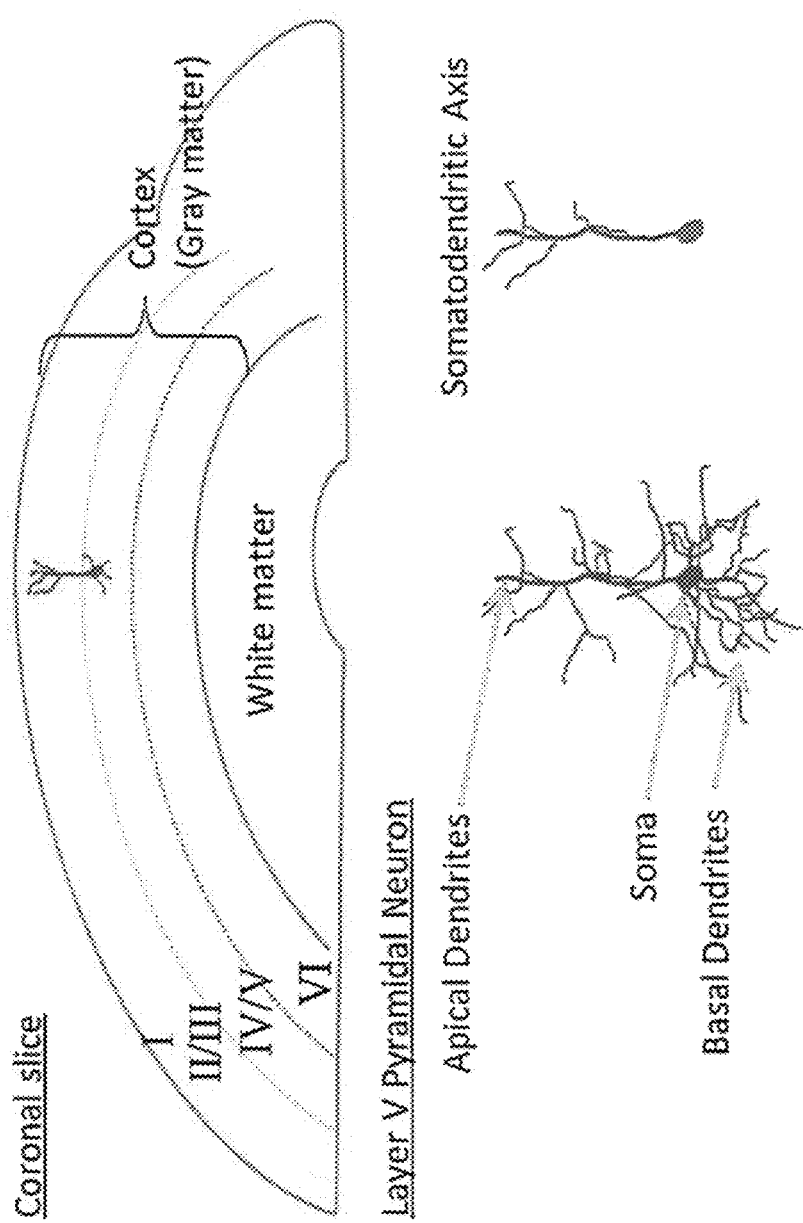
FIG. 6 is an illustration of cortical coronal slices (top) and the typical morphology of an excitatory pyramidal neuron (bottom) located in layer V, illustrating the location and orientation of the neuron's somatodendritic axis with respect to the slice.

In order to examine whether polarization along the neurons might modulate SD, brain slices were prepared and placed with the somatodendritic axis of principal cells (see FIG. 1 and FIG. 6) oriented in the direction of the polarizing field. This generates a gradient of polarization along the neuronal body from hyperpolarizing at one end to depolarizing at the opposite end. Simultaneous IOS and APG-2 imaging (see FIG. 1D-FIG. 1F) demonstrates the coincidence of the SD intrinsic signal with a concomitant transient decreasing intracellular K$^+$ signal consistent with experimental measurements (Brinley et al, 1960, Journal of Neurophysiology, 23(3), 246-56) and computational simulations (Wei et al., 2014, The Journal of Neuroscience, 34(35), 11733-43). Coronal slices maintain the integrity of the full depth of the gray matter, which permits anatomical exploration of polarization effects on cortex in analogous fashion to in vivo surface polarization where the somatodendritic axis is aligned with the applied field polarization (FIG. 6). While SD can be reliably produced in tangential cortical slices, which have the advantage of a more isotropic preparation of cortex (FIG. 4), the present studies utilize coronal slices in both high K+ and low K+ perfusates in order to study polarization effects on the intact layers of cortex.

Figure 5:
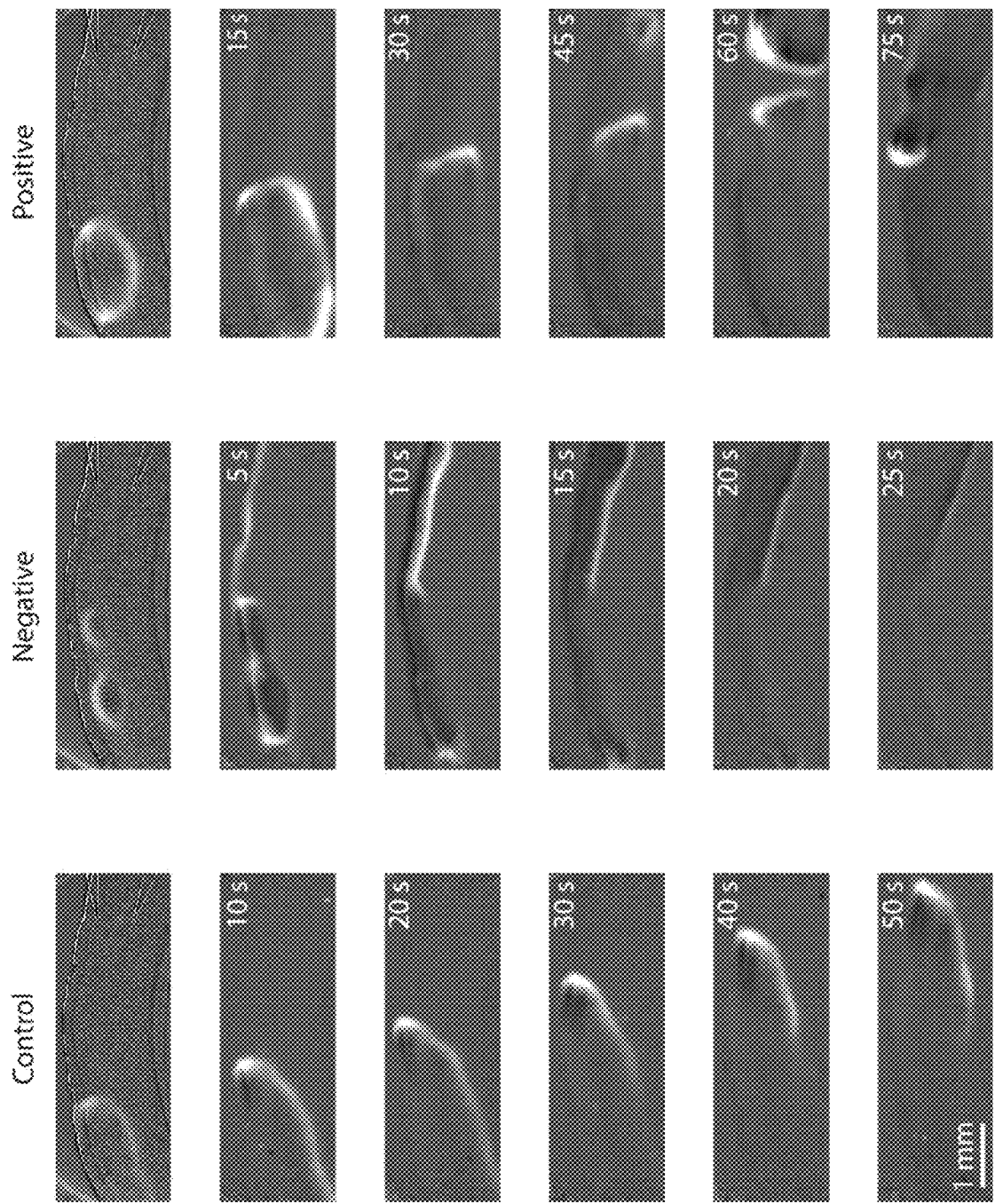
FIG. 5 depicts the electric field effects on the propagation and invasion of SD into the various layers of coronal slices evoked spontaneously in high $K^+$ bath perfusion (26 mM), imaged via IOS. Normal SD propagation through all cortical layers during a control trial (left). SD propagation under surface negative DC polarization (center) applied just before the second frame causes SD ignition to occur simultaneously across the uppermost cortical layers and propagation continues unabated. SD propagation was temporarily blocked from invading upper layers of cortex by surface positive DC polarization (right), which in high K+ bath caused a secondary SD wave ignition in the deeper layers of cortex (red arrow). Eventually the continuous cellular depolarization from high $K^+$ bath causes SD invasion to overcome the effects of polarization. Images contrast enhanced for display by background subtraction.

In high $K^+$ perfusion experiments, surface negative polarizations showed a dramatic near-simultaneous ignition of SD along the superficial layers in front of the wavefront, whereas positive polarizations prevented further SD invasion into the superficial half of the cortex for a brief time (FIG. 5). Within 30 seconds the high $K^+$ bath depolarization of those tissues overwhelmed the temporary blockage and SD collapsed inward on the unaffected region consuming the rest of the tissue (frames 5 and 6 in FIG. 5). Also notable in the lower right side of the fourth frame in FIG. 5 is a second SD wave ignition in deeper layers of the cortex caused by depolarization of the deeply located neuronal membranes by surface positive polarization in the presence of high bath $K^+$. These results indicate that the full effect of DC polarization of the cortex is counteracted by the global effects of excessively high $K^+$ bath perfusion on the cortical tissue.

Figure 2A:
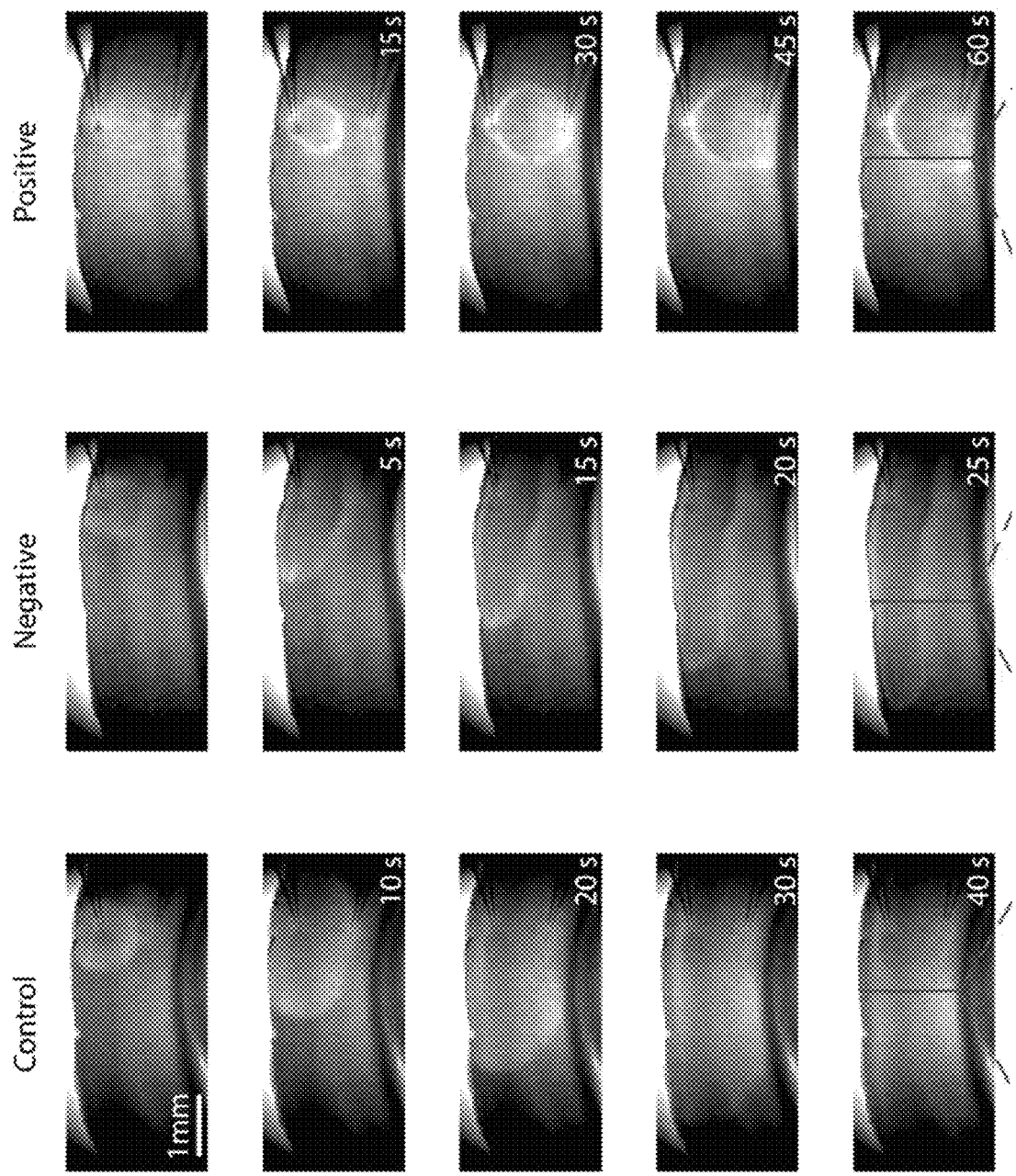
FIG. 2A and FIG. 2B, depicts the results of exemplary modulation experiments.
Figure 2B:
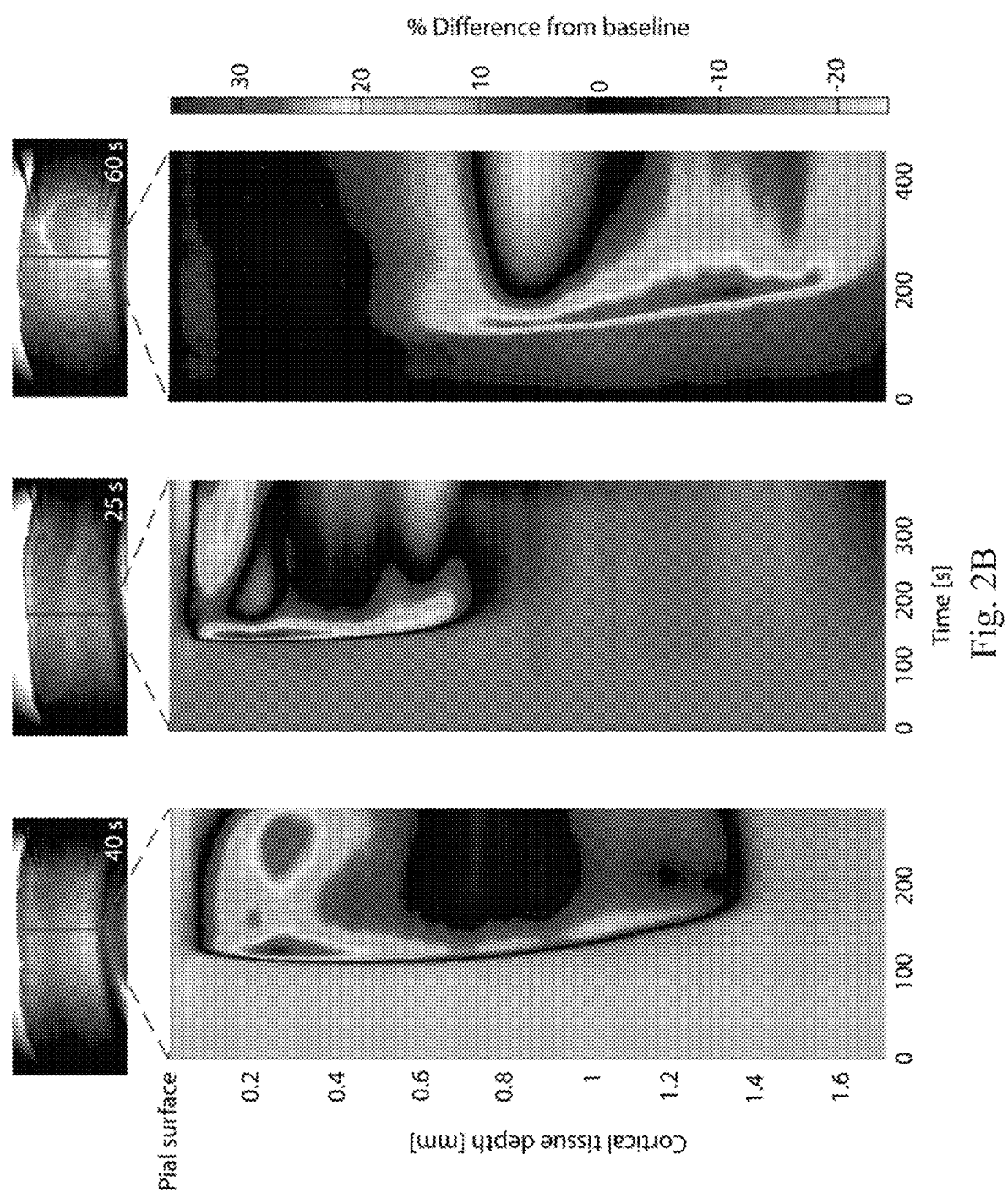

In brains of patients suffering from SD, the extracellular space is not known to have such pathologically high concentrations of $K^+$. Therefore a series of experiments were performed triggering SD with local high $K^+$ injection (Canals et al., 2005, Journal of Neurophysiology, 94(2), 943-51; Tottene et al., 2009, Neuron, 61(5), 762-73). This local injection of $K^+$ supports SD propagation in perfusates with much lower concentrations of $K^+$ (6.25 mM). FIG. 2 presents the effects of DC polarizations of the intact cortical gray matter in SD induced by local injections of high $K^+$. In FIG. 2A, the left column shows a control (unstimulated) trial with SD propagating along all layers of the cortex. The IOS wave in the deeper layers lags behind the propagating wave front in the superficial layers. The middle column shows that SD propagation is confined to the superficial layers of cortex under surface negative polarization. In the right hand column, surface positive polarization drives SD propagation toward the deeper layers of cortex where further horizontal spread is arrested and the wave slowly dissipates. A spatiotemporal analysis of the IOS SD signal in FIG. 2B illustrates different evolutions of the signal as a function of trial type and cortical depth. The leading edges of the SD peaks are located in the superficial layers with control or surface negative polarization. Surface negative polarization shrinks the spatial depth of the IOS signal to the superficial layers. Surface positive polarization demonstrates forcing of SD to the cortical depths whereby the SD IOS peak is more gradual in rise and prolonged in duration. The intracellular APG-2 epi-fluorescence (FIG. 1E and FIG. 1F), demonstrated that the decrease in intracellular $K^+$ concentration was tightly locked to the leading edge of the SD wavefronts.

Figure 3A:
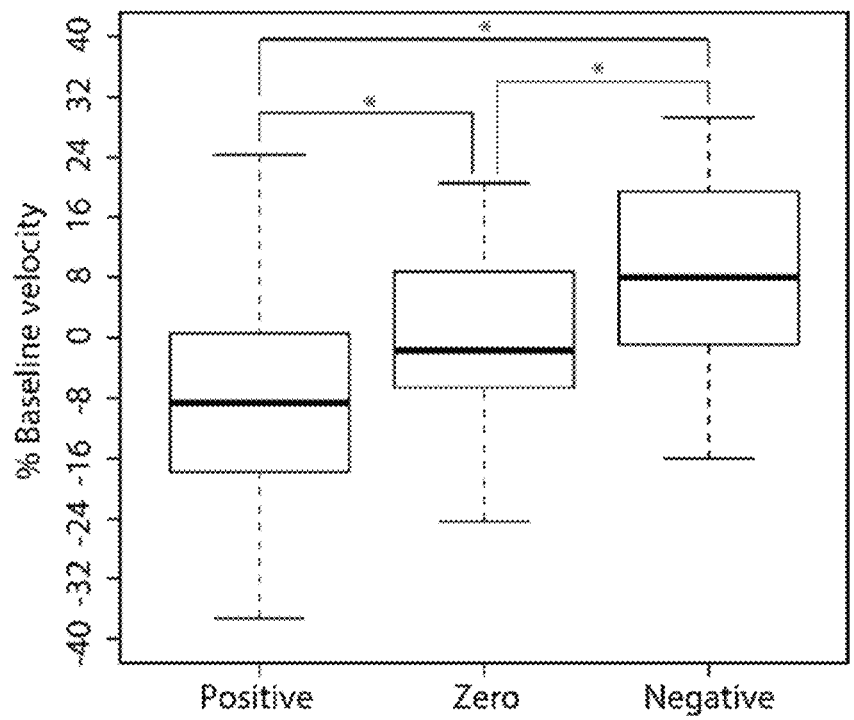
Figure 3B:
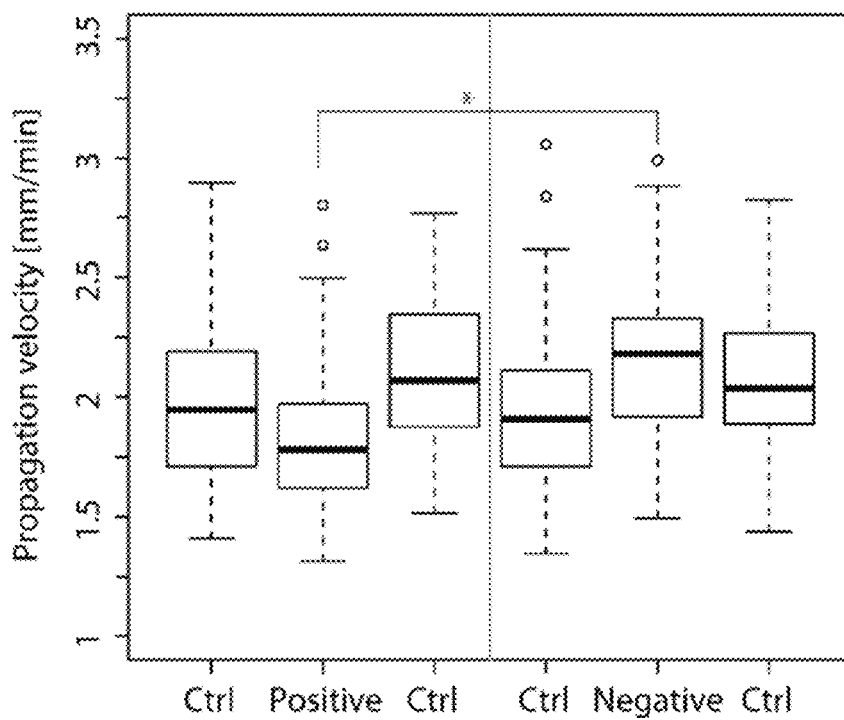

Analysis of the SD propagation velocities in FIG. 3A and FIG. 3B, indicated that surface positive polarization slowed while negative polarization increased propagation velocity (p<0.01, n=52). Dose response studies conducted on positive surface polarization field strength and delay time confirmed that as field strength increases and delay time shortens, the effective SD arrest rate increased and total SD affected areas decreased (FIG. 3C and FIG. 3D). The modulation of SD was proportional to the polarization of the somatodendritic axis for (n=32) SD events for each trial condition under surface positive polarization (FIG. 3D).

Note also in FIG. 3C the bimodal nature of the distributions at lower field strengths and longer delay times; indeed, SD propagations that were not arrested (grey dots) consumed more tissue on average than effective polarization trials at the same field strengths that arrested SD (black dots). Also, as the field strength increases from weak (54 mV/mm) to strong (216 mV/mm) polarization, the number of SD events arrested (out of 32) rose to 100% for field strengths greater than 160 mV/mm (FIG. 3C). The dose response curves and the rates of SD propagation arrest are shown to be consistent across a range of field strengths and delay times in FIG. 3D. It was also found that pre-polarization of the brain tissue in advance of the high $K^+$ injection could prevent the induction of SD in a field strength intensity-dependent manner (FIG. 3D).

In this work, experimental findings are reported demonstrating that polarization of the somatodendritic axis could be utilized to speed up, slow down, arrest and even prevent propagating waves of SD. Further, the polarity that blocks SD is opposite to that which suppresses spikes (Purpura and Malliani, 1966, Brain Research, 1(4), 403-6; Purpura and McMurtry, 1965, Journal of Neurophysiology, 28(1), 166-85; Bikson et al., 2001, The Journal of Physiology, 531(1), 181-191) and seizures (Gluckman et al., 1996, Journal of Neurophysiology, 76(6), 4202-5).

The IOS and K+ optical measurements presented herein suggests a dual effect on SD. First, intracellular hyperpolarization of the apical dendrites counteract SD triggering that depends upon depolarization of the dendrites (Kager et al., 2002, Journal of Neurophysiology, 88(5), 2700-12; Makarova et al., 2008, The European Journal of Neuroscience, 27(2), 444-56). Second, surface positive polarization act in an electrophoretic manner to drive extracellular positive charges including $K^+$ away from superficial dendritic membranes particularly sensitive to depolarization by extracellular $K^+$ during SD ignition. These two effects act synergistically to block further propagation of SD. The spatial extent of dendritic arborizations and high surface area to volume ratio of dendritic membranes in these superficial layers, combined with the relatively small extracellular volume fraction, contributes to their sensitivity to high concentrations of extracellular $K^+$ during the ignition and propagation of SD (de Luca and Bures, 1977, Developmental Psychobiology, 10(4), 289-97). The present results demonstrate the unexpected finding that this sensitivity explains the preference of SD to propagate along these layers as shown in FIG. 2 and FIG. 5.

While this may raise concerns over positive polarization eliciting a seizure as an unwanted side effect, the present data, despite mildly elevated K+ in the perfusate (6.5 mM) that helped support propagating SD, shows no overt evidence that seizures were generated by the surface negative polarizations. Control trials following surface negative polarizations demonstrated full tissue recovery and readily generated SD, whereas SD does not invade regions with active or recent seizure activity (Koroleva and Bures, 1979, Brain Research, 173(2), 209-15). Neurons involved with the SD wave front were likely inactivated by the local elevation in extracellular K+ causing depolarization block (Reddy and Bures, 1980, Neuroscience Letters, 17(3), 243-247).

The observation that surface positive polarization to arrest SD does not cause seizures under conditions where SD develops, and that surface negative polarization does not cause SD under conditions when seizures are generated and suppressed with electrical stimulation (Gluckman et al., 1996, Journal of Neurophysiology, 76(6), 4202-5; Gluckman et al., 2001, The Journal of Neuroscience, 21(2), 590-600; Bikson et al., 2001, The Journal of Physiology, 531(1), 181-191), demonstrates the novel finding that the control required to modulate either condition (SD or seizures) is state dependent. Indeed, recent work has demonstrated that there is a unification between spikes, seizures, and SD that are all part of the dynamical repertoire of the neuronal membrane, but that such activities are each confined to separate regions of the parameter space (ion concentrations, oxygenation, cell volume status) that defines which normal or pathological state might arise (Wei et al., 2014, The Journal of Neuroscience, 34(35), 11733-43). That each polarization polarity treatment does not produce the other pathological state implies that state-dependent observation can dictate state dependent control. The present results demonstrate that control of seizures or SD requires that the state of the brain tissue be estimated, so that the appropriate polarity and type of stimulation can be applied.

Control of SD may be placed within a broader context of state-based control. State-based control has two requirements. First, by sensing the state of a system, here in particular the brain, one needs to determine whether the brain tissue is in a normal steady-state, in a seizure state, or in a spreading depression state. It is also possible that the brain is in a mixture state of these states (Wei et al., 2014, The Journal of Neuroscience, 34(35), 11733-43). Based upon the state, the nature of the control applied needs to be uniquely defined. For instance, if the brain is in a seizure state, then the appropriate control stimulus applied to stop the seizures. If the brain is in an SD state, then the appropriate control stimulus needs to be applied to stop the SD. The polarity and nature of the control stimulus applied in either state can be completely different. In fact, the determination of state is critical, because the nature and polarity of the stimulus that would stop one of these pathological conditions can make the other state worse.

Furthermore, if the brain is in a normal, steady-state, or physiological state that is required for normal function, the task of state dependent observation and control is also different. In the normal state, the task of the controller is to maintain the steady state. The signal characteristics can be defined when sensing the brain to determine when it is close to the transition to a pathological state, such as the transition to seizures or SD, and apply control stimulation to avoid those critical transitions. Such avoidance of transitions, also called tipping points or bifurcations, may require additional unique control stimulation to maintain the steady state.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of modulating spreading depression (SD) in the brain of a subject comprising
    a) administering directly to the brain tissue an electric or magnetic stimulation of a selected surface polarization based on the orientation of the neurons to be affected; and
    b) modulating SD wave propagation in the brain via the administered electric or magnetic stimulation, wherein modulating SD wave propagation comprises one or more of: modulating the speed of SD wave propagation, arresting SD wave propagation, preventing the induction of SD wave propagation; or confining the spread of SD wave propagation.

2. The method of claim 1, wherein the step of administering a stimulation comprises administering an electric field directly to the brain tissue.

3. The method of claim 2, wherein the electric field has a strength of about 1 mV/mm to about 500 mV/mm.

4. The method of claim 1, wherein the stimulation slows or arrests SD propagation in the brain.

5. The method of claim 4, wherein the stimulation is administered in response to the detection of SD in the brain.

6. The method of claim 1, wherein the stimulation prevents SD initiation in the brain.

7. The method of claim 6, wherein the stimulation is administered in response to the detection of a signal or property of the brain indicative of the likelihood of a future SD wave.

8. The method of claim 6, wherein the stimulation is administered in response to the intention of a patient or health care provider.

9. The method of claim 1, wherein the subject has or is at risk of developing a disorder associated with SD, where the disorder is selected from the group consisting of migraine, stroke, hemorrhage, ischemia, hypoxia, seizures, epilepsy, postoperative brain surgery, and traumatic brain injury.

10. The method of claim 1, wherein the wherein the step of administering a stimulation comprises administering a magnetic field directly to the brain tissue.

11. The method of claim 1, wherein the selected surface polarization comprises a positive or negative polarization.

12. The method of claim 1, wherein the selected surface polarization comprises a surface positive polarization configured to modulate SD in the cortex.

13. The method of claim 1, wherein the selected surface polarization comprises a surface negative polarization configured to suppress seizure activity in the cortex.

14. The method of claim 1, wherein the selected surface polarization comprises a surface negative polarization configured to modulate SD in the hippocampus.

15. The method of claim 1, wherein the selected surface polarization comprises a surface positive polarization configured to suppress seizure activity in the hippocampus.

16. A method of state-dependent modulation of pathological neural activity comprising:
    a) detecting one or more signals or properties of the brain indicative of a pathological state of the brain;
    b) determining stimulation parameters based on the detected signals or properties;
    c) administering directly to the brain tissue an electric or magnetic stimulation of a selected surface polarization based on the orientation of the neurons to be affected consistent with the determined stimulation parameters; and
    d) reducing the pathological neural activity via the administered electric or magnetic stimulation.

17. The method of claim 16, wherein the selected surface polarization comprises a surface positive polarization configured to modulate SD in the cortex, a surface negative polarization configured to suppress seizure activity in the cortex, a surface negative polarization configured to modulate SD in the hippocampus, or a surface positive polarization configured to suppress seizure activity in the hippocampus.

18. The method of claim 16, wherein the detected one or more signals or properties of the brain indicative of the pathological state of the brain comprises at least one of:
    a neuronal network activity;

a membrane potential;
a presence or abundance of a biomarker;
an extracellular K+ concentration;
a presence or abundance of metabolic compound;
an adenosine concentration;
a glutamate concentration;
an electroencephalogram (EEG); and
a presence or abundance of normal or abnormal delta, theta, alpha, beta, gamma, or mu wave activity.

19. The method of claim 16, wherein the pathological state of the brain comprises a steady state, an SD state, a seizure state, or a mixed SD and seizure state.

20. The method of claim 19, wherein the pathological state of the brain is selected from the group consisting of: spreading depression, seizure, and a combination thereof.

* * * * *